United States Patent
Park et al.

(10) Patent No.: US 6,538,163 B2
(45) Date of Patent: Mar. 25, 2003

(54) METHOD FOR REDUCTION OF SUBSTITUTED MALONATES TO DIOLS

(75) Inventors: Won Suh Park, North Andover, MA (US); John Hiroshi Yamamoto, Haverhill, MA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 10/132,111

(22) Filed: Apr. 25, 2002

(65) Prior Publication Data

US 2003/0036666 A1 Feb. 20, 2003

Related U.S. Application Data

(60) Provisional application No. 60/290,434, filed on May 11, 2001.

(51) Int. Cl.$^7$ .................. C07C 29/147; C07C 31/20
(52) U.S. Cl. .................. 568/852; 568/853; 568/864
(58) Field of Search ............... 568/852, 853, 568/864

(56) References Cited

U.S. PATENT DOCUMENTS

| | | |
|---|---|---|
| 3,660,416 A | 5/1972 | Vit |
| 4,096,192 A | 6/1978 | Bhatia et al. |
| 4,250,337 A | 2/1981 | Zur Hausen et al. |
| 4,317,945 A | 3/1982 | Bernhagen et al. |
| 4,762,947 A | 8/1988 | Ninomiya et al. |
| 4,868,327 A | 9/1989 | Stiefel |
| 4,982,016 A * | 1/1991 | Choi ................ 568/814 |
| 5,072,056 A | 12/1991 | Stiefel |
| 5,091,595 A * | 2/1992 | Choi ................ 568/814 |
| 5,395,989 A | 3/1995 | Yoneoka et al. |
| 5,500,484 A | 3/1996 | Iwasaki et al. |

OTHER PUBLICATIONS

Database CAPLUS on STN, Acc. No. 1992:553148, Prokhorenko et al., Zh. Prikl. Khim. (S.–Peterburg) (1991), 64(4), p. 941–4 (abstract).*
Finholt, A.E. et al., Organic Reductions by Sodium Aluminum Hydride, J. Am. Chem. Soc., vol. 77, No. 15, p. 4163, (1955).
Pitha, J. et al., Uber die Reduktion der Carbonsauren und ihrer Derivate mit Natriumaluminiumhydrid, Collect. Czech. Chem. Commun., vol. 25, pp. 736–742, (1960).
Bogatskii, A. V. et al., Macroheterocylcles. XI. The stereospecificity of the reduction of ethyl isopropylacetoacetate by complex dydrides in the presence of dibenz–18–crown–6., J. Org. Chem. USSR (Engl. Transl.), vol. 17, No. 6, pp. 1062–1064, (1981).
Jin Soon Cha et al., Organic Preparations and Procedures Int., Reduction of Organic Compounds with Sodium Aluminium Hydride in Theoretical Amount, vol. 26 (4) pp. 459–464 (1994).
Jin Soon Cha et al., J. Org. Chem., Reaction of Sodium Aluminum Hydride with Selected Organic Compounds Containing Representative Functional Groups. Comparison of the Reducing Characteristics of Lithium and Sodium Aluminum Hydrides, vol. 58 No. 17 pp. 4727–4731 (1993).

* cited by examiner

*Primary Examiner*—Brian Davis
(74) *Attorney, Agent, or Firm*—Kenneth Crimaldi

(57) ABSTRACT

A method for reducing a malonate having the formula $R^1R^2C(CO_2R^3)(CO_2R^4)$ to a diol having the formula $R^1R^2C(CH_2OH)_2$ comprising treating said malonate with sodium aluminum hydride.

8 Claims, No Drawings

METHOD FOR REDUCTION OF SUBSTITUTED MALONATES TO DIOLS

CROSS REFERENCE TO RELATED PATENT APPLICATIONS

This is a non-provisional application of prior pending U.S. provisional application Ser. No. 60/290,434 filed May 11, 2001.

BACKGROUND

This invention relates generally to a method for reducing substituted malonates to diols using sodium aluminum hydride.

Substituted malonates have been reduced to the corresponding diols with lithium aluminum hydride or with lithium borohydride, as described in U.S. Pat. No. 4,982,016. However, reduction of substituted malonates with sodium aluminum hydride has not been reported.

Sodium aluminum hydride typically is available commercially as a slurry in toluene at a lower cost than lithium aluminum hydride or lithium borohydride. A method for reducing substituted malonates to diols, without using lithium aluminum hydride or lithium borohydride would be more economical and would be commercially valuable.

STATEMENT OF INVENTION

The present invention is directed to a method for reducing a malonate of formula $R^1R^2C(CO_2R^3)(CO_2R^4)$ to a diol of formula $R^1R^2C(CH_2OH)_2$ comprising treating said malonate with sodium aluminum hydride; wherein $R^1$ is aryl, alkyl, aralkyl, alkenyl, or alkynyl; $R^2$ is hydrogen, aryl, alkyl, alkenyl, or alkynyl; and $R^3$ and $R^4$ are independently alkyl or aralkyl.

DETAILED DESCRIPTION

Unless otherwise specified, all percentages herein are stated as weight percentages, temperatures are in ° C., and volumes in mL.

An "alkyl" group is a saturated hydrocarbyl group having from one to twenty carbon atoms in a linear, branched or cyclic arrangement. Preferably, alkyl groups have from one to twelve carbon atoms, and most preferably, from one to six carbon atoms. An "alkenyl" group is an "alkyl" group in which at least one carbon-carbon single bond has been replaced with a double bond. An "alkynyl" group is an "alkyl" group in which at least one carbon-carbon single bond has been replaced with a triple bond. Preferably, alkyl, alkenyl and alkynyl groups are acyclic and unsubstituted. Alkyl, alkenyl and alkynyl groups optionally are substituted with one or more hydroxy, halo, alkyl, alkenyl, alkoxy, amino or alkylamino groups, with substitution by one or more halo groups being possible on alkyl or alkoxy groups. An "aryl" group is a substituent derived from an aromatic compound, including heterocyclic aromatic compounds having at least one nitrogen, oxygen or sulfur atom in the ring. An aryl group has a total of from five to twenty ring atoms, and has one or more rings which are separate or fused. Preferably, aryl groups have from five to ten ring atoms. Substitution on aryl groups of one or more hydroxy, halo, alkoxy, alkyl, alkenyl or alkynyl groups is permitted, with substitution by one or more halo groups being possible on alkyl, alkenyl or alkoxy groups. An "aralkyl" group is an "alkyl" group substituted by an "aryl" group.

In one embodiment of the invention, $R^1$ is aryl and $R^2$ is hydrogen. Preferably, $R^1$ is phenyl and $R^3$ and $R^4$ are alkyl, i.e., the substituted malonate is a dialkyl phenylmalonate. $R^3$ and $R^4$ represent the same alkyl group or different alkyl groups. The 2-phenyl-1,3-propanediol product obtained in this embodiment is useful as an intermediate for the corresponding diol dicarbamate compound, an important intermediate in the dye industry and in pharmaceutical applications. In another embodiment of the invention, $R^1$ and $R^2$ are alkyl, wherein $R^1$ and $R^2$ are the same or different alkyl groups. Preferably, $R^1$ and $R^2$ are n-butyl and $R^3$ and $R^4$ are alkyl, wherein $R^3$ and $R^4$ are the same or different alkyl groups.

Typically, the method of this invention is performed in an ethereal solvent in which sodium aluminum hydride is soluble, for example, tetrahydrofuran ("THF") or glymes. Suitable glymes include, for example, monoglyme (dimethoxyethane), diglyme (2-methoxyethyl ether), triglyme (triethylene glycol dimethyl ether), and tetraglyme (tetraethylene glycol dimethyl ether). The preferred solvent is THF. The preferred temperature range for the reduction is from −90° C. to 150° C., more preferably from 25° C. to 90° C., and most preferably from 40° C. to 75° C. The reduction reaction is continued until the substituted malonate starting material has been substantially consumed. The preferred reaction time is from 0.1 hours to 48 hours, more preferably from 6 hours to 40 hours, and most preferably from 8 hours to 30 hours. Preferably, the amount of SAH, relative to the amount of malonate, is from 1 to 10 equivalents, more preferably from 1 to 5 equivalents, and most preferably from 1 to 2 equivalents. In one embodiment of the invention, sodium aluminum hydride ("SAH") is introduced in the form of a slurry comprising SAH and toluene. Preferably, the slurry has from 1% to 75% SAH and from 25% to 99% toluene, more preferably from 10% to 60% SAH and from 40 to 90% toluene, and most preferably from 30% to 50% SAH and from 50% to 70% toluene.

EXAMPLE

Conversion of Diethyl 2,2-Dibutylmalonrate to 2,2-Dibutyl-1,3-propanediol

An oven-dried 1000 mL three-neck flask containing a magnetic stir bar was purged with nitrogen gas and charged with 30 g of sodium aluminum hydride and 250 mL of anhydrous tetrahydrofuran ("THF"). To this solution was added drop-wise, so that the reaction temperature remained below 60° C., a solution of 100 g diethyl 2,2-dibutylmalonate in 150 mL of THF. After completion of the addition (3–4 hours), the reaction mixture was heated to 50° C. and maintained at that temperature for 24 hours, after which the solution was cooled to room temperature. Methanol was added drop-wise until all of the excess aluminum hydride had been consumed, followed by 350 mL of saturated aqueous sodium chloride solution. The resulting mixture was separated and extracted three times with 250 mL portions of THF, and the combined THF layers were dried over anhydrous magnesium sulfate for five hours. The solvent was removed in vacuo, resulting in a slightly yellow syrupy sample. To this sample was added 100 g hexane, followed by removal of the solvent in vacuo. The residue was placed in a freezer at −22° C., where after a few hours, the sample solidified. Hexane (5 g) was added to the solid, which was then collected on a glass frit filter and washed with two ten-gram portions of hexane. The crystals were dried in air. Subsequent freezing of the filtrate produced two more crops of crystals, and addition of small amounts of hexane to the filtrate followed by freezing produced another two crops.

| | |
|---|---|
| Fraction 1 | 36.21 g |
| Fraction 2 | 16.48 g |
| Fraction 3 | 1.51 g |
| Fraction 4 | 3.80 g |
| Fraction 5 | 0.8 g |
| Total (% yield) | 58.8 g (85.2%) |

The results from the Example, and from additional reduction experiments are summarized in the following Table. Each experiment started with 100 g of diethyl 2,2-dibutylmalonate and used THF as a solvent, or a mixture of THF and toluene in cases where the metal hydride is used in the form of a toluene slurry. The metal hydrides used were sodium aluminum hydride ("SAH"), lithium aluminum hydride ("LAH"), sodium bis-(2-methoxyethoxy)aluminum hydride ("SDMA") or lithium borohydride ("LBH") with trimethoxyborate ("TMB"). Reaction times are given in hours, and reaction temperatures in ° C., as "reflux" (reflux temperatures not measured), or as "r.t." (room temperature).

TABLE

| Metal Hydride | Amount (equiv.) | Reaction Temp. | Reaction Time | Crude Weight | % Yield |
|---|---|---|---|---|---|
| SAH | 1 | 50° C. | 8 | 36.1 g | 58 |
| SAH | 1.5 | 50° C. | 12 | 51.75 g | 75 |
| SAH | 2 | 50° C. | 24 | 58.8 g | 85.2 |
| 45% SAH/ toluene | 1.5 | 50° C. | 24 | 61.42 g | 89.00 |
| LAH | 1 | 50° C. | 24 | 22.65 g | 32.82 |
| 45% LAH/ toluene | 1.5 | 50° C. | 24 | 28.49 g | 41.28 |
| LAH | 2 | 50° C. | 24 | 50.66 g | 73.40 |
| SDMA | 2 | r.t. | 22 | — | 25[1] |
| SDMA/ toluene | 2 | reflux | 6 | — | 39[1] |
| SDMA | 2 | reflux | 9 | — | 32[1] |
| LBH/ 0.2 TMB | 2 | 60° C. | 18 | — | 0.00 |

[1]. Yield determined by gas chromatography; product not isolated.

What is claimed is:

1. A method for reducing a malonate of formula $R^1R^2C(CO_2R^3)(CO_2R^4)$ to a diol of formula $R^1R^2C(CH_2OH)_2$ comprising treating said malonate with sodium aluminum hydride; wherein $R^1$ is aryl; $R^2$ is hydrogen, aryl, alkyl, alkenyl, or alkynyl; and $R^3$ and $R^4$ are independently alkyl or aralkyl.

2. The method of claim 1 in which $R^2$ is hydrogen or alkyl.

3. The method of claim 2 in which $R^2$ is hydrogen.

4. The method of claim 3 in which $R^1$ is phenyl and $R^3$ and $R^4$ are alkyl.

5. The method of claim 4 in which $R^3$ and $R^4$ are ethyl.

6. A method for reducing a malonate of formula $R^1R^2C(CO_2R^3)(CO_2R^4)$ to a diol of formula $R^1R^2C(CH_2OH)_2$ comprising treating said malonate with sodium aluminum hydride; wherein $R^1$ is linear or branched alkyl; $R^2$ is linear or branched alkyl; and $R^3$ and $R^4$ are independently alkyl or aralkyl.

7. The method of claim 6 in which $R^1$ and $R^2$ are n-butyl and $R^3$ and $R^4$ are alkyl.

8. The method of claim 7 in which $R^3$ and $R^4$ are ethyl.

\* \* \* \* \*